(12) United States Patent
Sugiura (10) Patent No.: US 8,855,382 B2
(45) Date of Patent: Oct. 7, 2014

(54) MRI MAMMOGRAPHY WITH FACILITATED COMPARISON TO OTHER MAMMOGRAPHY IMAGES

(75) Inventor: Satoshi Sugiura, Otawara (JP)

(73) Assignees: Kabushiki Kaisha Toshiba, Minato-Ku, Tokyo (JP); Toshiba Medical Systems Corporation, Otawara-Shi, Tochigi-Ken (JP)

(*) Notice: Subject to any disclaimer, the term of this patent is extended or adjusted under 35 U.S.C. 154(b) by 400 days.

(21) Appl. No.: 13/064,530

(22) Filed: Mar. 30, 2011

(65) Prior Publication Data

US 2011/0243418 A1 Oct. 6, 2011

(30) Foreign Application Priority Data

Mar. 30, 2010 (JP) .................................. 2010-77630
Mar. 28, 2011 (JP) .................................. 2011-69151

(51) Int. Cl.
*G06K 9/00* (2006.01)
*A61B 5/00* (2006.01)
*G01R 33/56* (2006.01)
*A61B 5/055* (2006.01)

(52) U.S. Cl.
CPC .......... *G01R 33/5608* (2013.01); *A61B 5/7425* (2013.01); *A61B 5/055* (2013.01)
USPC ........... 382/128; 382/131; 382/132; 382/133; 382/154

(58) Field of Classification Search
USPC .................................. 382/128, 131, 132, 154
See application file for complete search history.

(56) References Cited

U.S. PATENT DOCUMENTS

| 6,606,400 | B1 | 8/2003 | Takeo | |
|---|---|---|---|---|
| 7,828,732 | B2* | 11/2010 | Wang et al. | 600/437 |
| 7,885,443 | B2* | 2/2011 | Zingaretti et al. | 382/128 |
| 8,126,226 | B2* | 2/2012 | Bernard et al. | 382/128 |
| 8,135,452 | B2* | 3/2012 | Dougherty et al. | 600/420 |
| 2008/0292164 | A1* | 11/2008 | Azar et al. | 382/131 |
| 2009/0143668 | A1* | 6/2009 | Harms et al. | 600/410 |
| 2010/0022881 | A1* | 1/2010 | Fujita et al. | 600/445 |
| 2011/0150313 | A1* | 6/2011 | Su et al. | 382/132 |

OTHER PUBLICATIONS

C. Kuhl, "The Current Status of Breast MR Imaging, Part 1, Choice of Technique, Image Interpretation, Diagnostic Accuracy, and Transfer to Clinical Practice," *Radiology*, vol. 244, No. 2, pp. 356-378 (Aug. 2007).
E. Haacke, et al., "Physical Principles and Sequence Design," *Magnetic Resonance Imaging*, Chapter 23, pp. 697-700 (1999).

* cited by examiner

*Primary Examiner* — Tom Y Lu
(74) *Attorney, Agent, or Firm* — Nixon & Vanderhye PC (57) ABSTRACT

An image processing method generates two-dimensional images, each of which are respectively in accordance with left and right breasts of a subject using three-dimensional image data of the left and right breasts. A comparison two-dimensional combined image is generated, wherein the left and right breast images are disposed symmetrically. The comparison two-dimensional combined image is displayed on a display unit.

22 Claims, 7 Drawing Sheets

MRI MAMMOGRAPHY WITH FACILITATED COMPARISON TO OTHER MAMMOGRAPHY IMAGES

CROSS-REFERENCE TO RELATED APPLICATIONS

This application is based upon and claims the benefit of priority from Japanese Patent Application No. 2010-77630, filed Mar. 30, 2010, and Japanese Patent Application No. 2011-69151, filed Mar. 28, 2011, the entire contents of both of which are incorporated herein by reference.

FIELD

Exemplary embodiments described herein relate generally to image processing method and apparatus—and more particularly to breast magnetic resonance imaging (MRI) processing techniques.

BACKGROUND

A magnetic resonance imaging (MRI) apparatus is an apparatus which acquires chemical and physical micro-information of a substance utilizing a phenomenon whereby a target nuclear spin population, when placed in a magnetic field, resonates with a high-frequency magnetic field rotating at a specific frequency (resonant frequency) in accordance with the intrinsic magnetic moment and existing magnetic field intensity of the magnetic field, and generates a signal (a nuclear magnetic resonance (NMR) signal) in a nuclear spin relaxation process.

Such an MRI apparatus can acquire images of regions of the whole body, such as the head and neck, the abdomen and the spine. For this reason, it is often the case that the images acquired by the MRI apparatus are utilized for the purpose of diagnosis. Also, in recent years, MRI apparatus has been used to examine breasts too. It is reported that breast images acquired by MRI apparatus are particularly effective in early detection of breast cancer, diagnosing whether a lesion is benign or malignant, and diagnosing spread of a tumor.

However, with common image diagnosis of mammary gland disease, examination by X-ray mammography is typically first selected for reasons of diagnostic evidence, prevalence of such apparatus, and ease of examination. As a secondary choice, an examination by ultrasound diagnostic apparatus may typically also be made. It is also now often the case that an MRI examination is complementarily utilized—when determining whether or not a tumor mass has spread, with reference to an earlier image diagnosis by X-ray mammography or ultrasound.

DETAILED DESCRIPTION

First, an overall configuration of a typical MRI apparatus will be described. As those in the art will recognize, a conventional MRI apparatus can be configured (e.g., by loading and executing appropriate computer program modules into suitable digital computer program memory) to effect the various functional blocks to be described below and/or special application hardware (e.g., an ASIC (application specific integrated circuit)) can be configured to effect the various functional blocks to be described below. The following description of exemplary basic MRI apparatus will be understood as merely a high-level simplified description of a non-limiting example.

Figure 1:
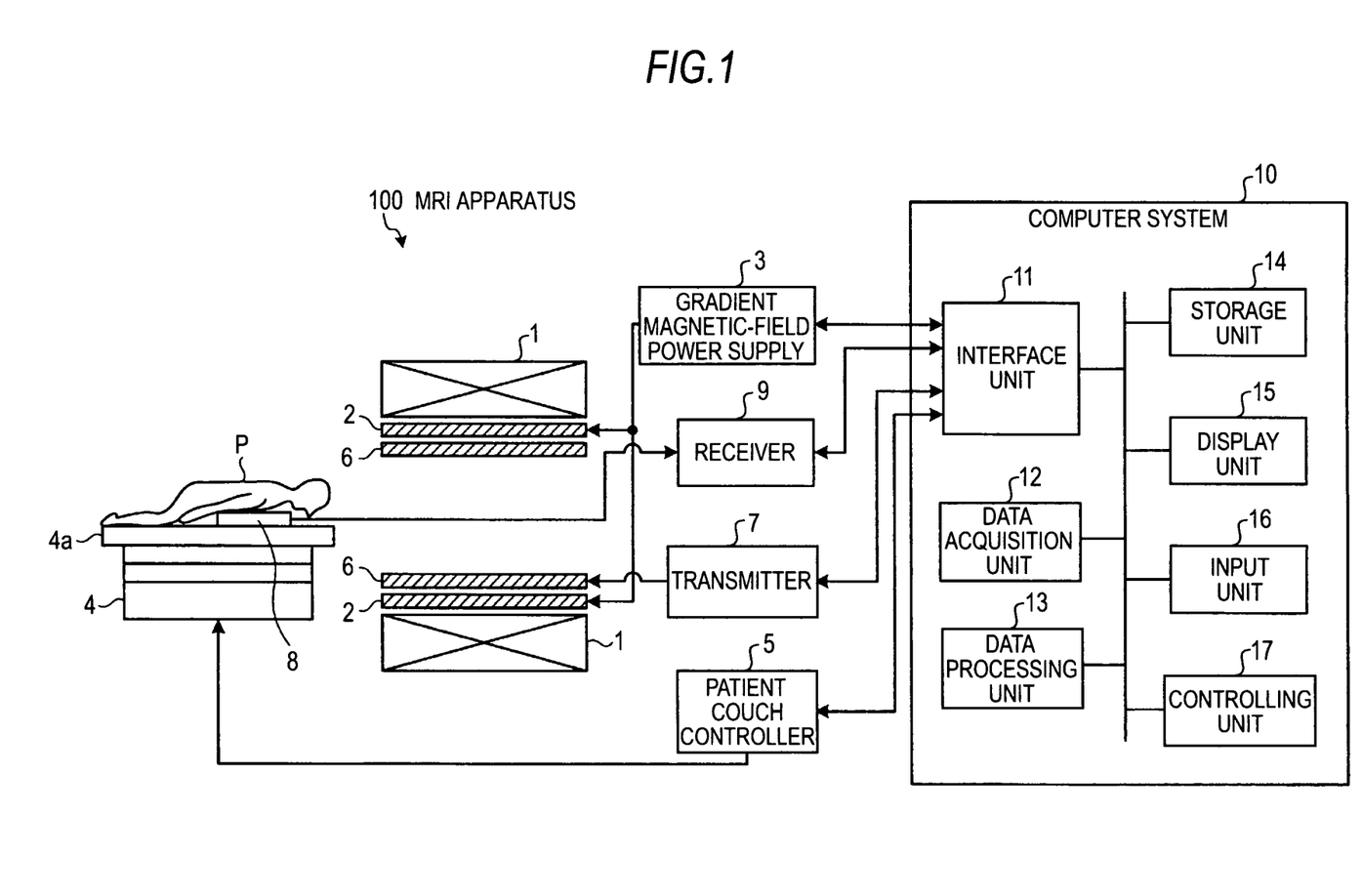
FIG. 1 is a simplified schematic block diagram of an exemplary embodiment of MRI apparatus.

FIG. 1 is a block diagram of MRI apparatus 100 which includes: a static magnetic-field magnet 1, a set of orthogonal gradient magnetic-field coils 2, controllable gradient magnetic-field power supplies 3, patient couch 4, patient couch controller 5, RF transmission coil 6, RF transmitter 7, RF reception coil 8, RF receiver 9 and computer system 10.

The static magnetic-field magnet 1 can, for example, comprise a hollow, cylindrical magnet structure that generates a substantially uniform static magnetic field in an imaging volume space within the static magnetic-field magnet 1. The static magnetic-field magnet 1 can include, for example, one or more permanent magnets, a superconductive magnet, and the like.

The set of gradient magnetic-field coils 2 can also comprise hollow, cylindrical coils disposed on an inner side of the static magnetic-field magnet 1. The set of gradient magnetic-field coils 2 may be formed by an assembly of three coils corresponding to each of the usual orthogonal axes, X, Y and Z (i.e., which axes are each perpendicular to one another). The three coils individually receive an electric current supplied by the gradient magnetic-field power supplies 3, described hereafter, and generate respective gradient magnetic fields of which magnetic field intensities respectively change along the X, Y and Z axes. By convention, typically the Z-axis direction chosen to be along same direction as the static magnetic-field magnetic field B0.

Here, as is typical, the x-axis gradient magnetic field corresponds to the read-out (Gr) direction, the y-axis gradient magnetic field corresponds to the phase-encoding (Ge) direction and the z-axis gradient magnetic field corresponds to the slice select (Gs) direction. The slice-selection gradient magnetic-field Gs is used to select any arbitrarily desired imaging cross-sectional slice. The phase-encoding direction gradient magnetic-field Ge is mainly used to change the phase of an NMR response signal as a function of resonant nuclei spatial position (in the y-axis direction). The readout gradient direction magnetic-field Gr is used to change the frequency (i.e., to frequency encode) of an NMR response signal as a function of resonant nuclei spatial position (in the x-axis direction). As will be appreciated, this assignment of conventional orthogonal directions can be changed.

The gradient magnetic-field power supplies 3 respectively supply the electric current to the individual gradient magnetic-field coils.

The patient couch 4 includes a top plate 4a on which a patient subject P is placed. Under control of the patient couch controlling unit 5, the top plate 4a is inserted into a cavity (opening to the imaging volume) within the static and gradient magnetic-field coils. Ordinarily, patient couch 4 is set such that a longitudinal direction of the patient couch 4 is parallel with a center axis of the static magnetic-field magnet 1.

The patient couch controlling unit 5 controls the patient couch 4. The patient couch controlling unit 5 drives the patient couch 4 and can move the top plate 4a in both the longitudinal and vertical directions.

RF transmission coil 6 is disposed radially inwardly of the gradient magnetic field coils. The RF transmission coil 6 receives high-frequency (RF) pulses from transmitter 7 and generates corresponding high-frequency (RF) magnetic fields B1.

The RF transmitter 7 transmits the high-frequency RF pulse at a frequency corresponding to the Larmor frequency of a desired nuclei species via RF transmission coil 6.

The RF reception coil 8 receives a NMR RF response signal emanating from the subject P as induced to occur by the transmitted RF pulse. The RF reception coil 8 of present exemplary embodiments is for breast imaging, which is set on the top plate 4a of the couch 4. Procumbent subject P is placed upon the RF reception coil 8 while imaging. Upon receiving the NMR RF signal, the RF reception coil 8 outputs received NMR signals to RF receiver 9.

The RF receiver 9 generates detected NMR data for k-space based on the RF NMR signal outputted from RF reception coil 8. The RF receiver 9 transmits the generated NMR signal to computer system.

The computer system 10 performs overall control of the MRI apparatus 100, collects data, reconstructs images, and the like. The computer system 10 can typically include interface unit 11, data acquisition unit 12, data processing unit 13, storage unit 14, display unit 15, input unit 16 and controlling unit 17.

The interface unit 11 controls input and output of various signals exchanged between the computer system 10 and the controllable gradient magnetic-field power supplies 3, the patient couch controller 5, the RF transmitter 7 and RF receiver 9.

The data acquisition unit 12 acquires NMR signal transmitted from the RF receiver 9 via the interface unit 11. The acquired NMR signal is stored in the storage unit 14.

The data processing unit 13 performs post-processing, namely, image reconstruction using processes such as multi-dimensional Fourier Transform, on the NMR signal data stored in storage unit 14. As a result, the data processing unit 13 generates a display image.

Storage unit 14 stores NMR signal data received by the data acquisition unit 12, image data generated by the data processing unit 13, and the like.

Display unit 15 displays various pieces of information under control of controlling unit 17. A display device such as a liquid crystal display (LCD) device can be used as display unit 15.

Input unit 16 receives various instructions and pieces of information input by an operator. Pointing devices such as a mouse and/or a track ball, and/or an input device such as a keyboard can be used accordingly as input unit 16.

Controlling unit 17 may include a central processing unit (CPU) (not shown), a memory, and the like to perform overall control of MRI apparatus 100. Specifically, the controlling unit 17 may executes various acquisition sequences based on imaging conditions set by operator, thereby controlling the controllable gradient magnetic-field power supplies 3, the RF transmitter 7 and RF receiver 9.

Heretofore, a description has been given of an overall configuration of the MRI apparatus according to an exemplary embodiment. With this kind of configuration, the computer system 10 executes an imaging sequence to acquire an MR signal from a three-dimensional space including the left and right breasts of the subject P. Also, the computer system 10 reconstructs three-dimensional image data of the left and right breasts based on the MR signal acquired by executing the imaging sequence. Also, the computer system 10 generates two-dimensional images, one each of the left and right breasts, from the reconstructed three-dimensional image data and, by suitably rotating (and possibly combining chest wall portions of) the generated two-dimensional images, generates a two-dimensional image wherein the left and right breasts are disposed symmetrically (e.g., in a fashion similar or identical to traditional X-ray mammography depiction). Then, the computer system 10 causes the display unit 15 to display the generated two-dimensional image.

Herein, with the heretofore known MRI technology, it has not been possible to easily compare an X-ray mammography image and an image imaged by the MRI apparatus. For example, in standard X-ray mammary diagnostic imaging, there are cranio-caudal (CC) direction images and medio-lateral (ML) direction images or medio-lateral oblique (MLO) direction images. Then, in general, right and left breast images imaged separately by these techniques are displayed side-by-side (in opposite directions) for reading (e.g., with the chest walls combined) in order to easily see symmetries.

Meanwhile, MRI apparatus can acquire three-dimensional breast image data. For this reason, in an MRI examination, normally, an axial image or a sagittal image, or an MIP (maximum intensity projection) image in the axial and sagittal directions, is used for diagnostic reading. Consequently, when reading an MRI image in comparison with an X-ray mammography image, the line of sight and orientation of display for one of the images differs from those of the other mage being compared, meaning that it is difficult for a reader to comprehend a proper positional relationship between the two.

However, according to an exemplary embodiment, left and right breast images imaged by the MRI apparatus 100 are displayed in a condition in which the left and right breasts are disposed symmetrically—possibly, if desired, even having the chest walls from these two images combined in the same way as traditionally done in X-ray mammography images. Consequently, in the case of comparing an MR image with an X-ray mammography image, the line of sight and orientation of display for each image are the same, meaning that it is possible for the reader to more easily comprehend positional relationships between the two. That is, according to the exemplary embodiment, it is possible to provide the reader with an MR image which can be easily more easily compared with an X-ray mammography image.

Hereafter, a description will be given of more details of the MRI apparatus 100, now centered on the function of computer system 10. Hereafter, a two-dimensional image generated by the computer system 10, that is, a two-dimensional image wherein the left and right breasts are disposed symmetrically (and in this example by also combining chest wall portions of the two-dimensional images of the left and right breasts), will be called a "comparison breast image" (CBI).

Figure 2:
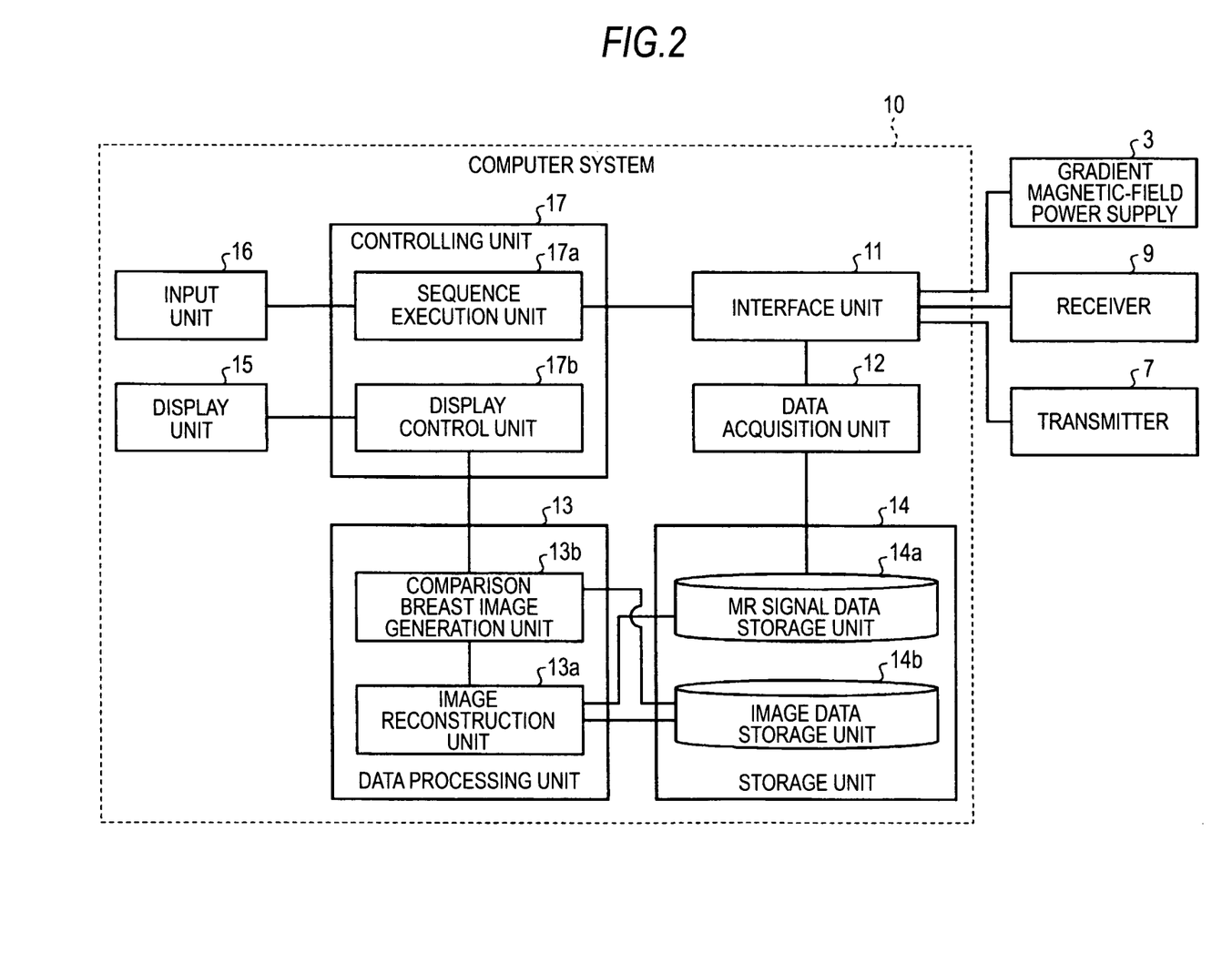
FIG. 2 is a simplified schematic functional block diagram of the computer system of FIG. 1.

FIG. 2 is a functional block diagram showing a more detailed configuration of the exemplary computer system 10. A description will now be given centered on functions relating to the data processing unit 13, storage unit 14 and controlling unit 17 shown in FIG. 1.

As shown in FIG. 2, the storage unit 14 has an MR signal data storage unit 14a and an image data storage unit 14b. The MR signal data storage unit 14a stores MR signal data acquired by the data acquisition unit 12. Also, the image data storage unit 14b stores the image data generated by the data processing unit 13.

Also, the controlling unit 17 has a sequence execution unit 17a and a display control unit 17b. The sequence execution unit 17a executes various imaging sequences by generating various sequence execution data based on the imaging conditions set by the operator, and controlling the gradient magnetic-field power supply 3, transmitter 7 and receiver 9 in accordance with the generated sequence execution data. The sequence execution data used herein are information defining a procedure for executing imaging, such as strength of the electric current supplied to the gradient magnetic-field coils 2 by the gradient magnetic-field power supply 3 and timing for supplying the electric current, strength of the RF signal transmitted to the RF transmission coils 6 by transmitter 7 and timing for transmitting the RF signal, and timing at which receiver 9 detects the NMR signal. The display control unit 17b causes the display unit 15 to display the CBI generated by a comparison breast image generation unit 13b to be described hereafter.

Also, the data processing unit 13 has an image reconstruction unit 13a and the CBI generation unit 13b. The image reconstruction unit 13a reconstructs the three-dimensional image data of the left and right breasts of the subject P based on the MR signal data acquired by executing the imaging sequence for acquiring the magnetic resonance signal from the three-dimensional space including the left and right breasts of the subject. The comparison breast image generation unit 13b generates a two-dimensional image wherein the two-dimensional images of the left and right breasts of the subject P are disposed symmetrically with the chest wall sides of the breasts combined (in this particular example) as the CBI from the three-dimensional image data reconstructed by the image reconstruction unit 13a.

Figure 3:
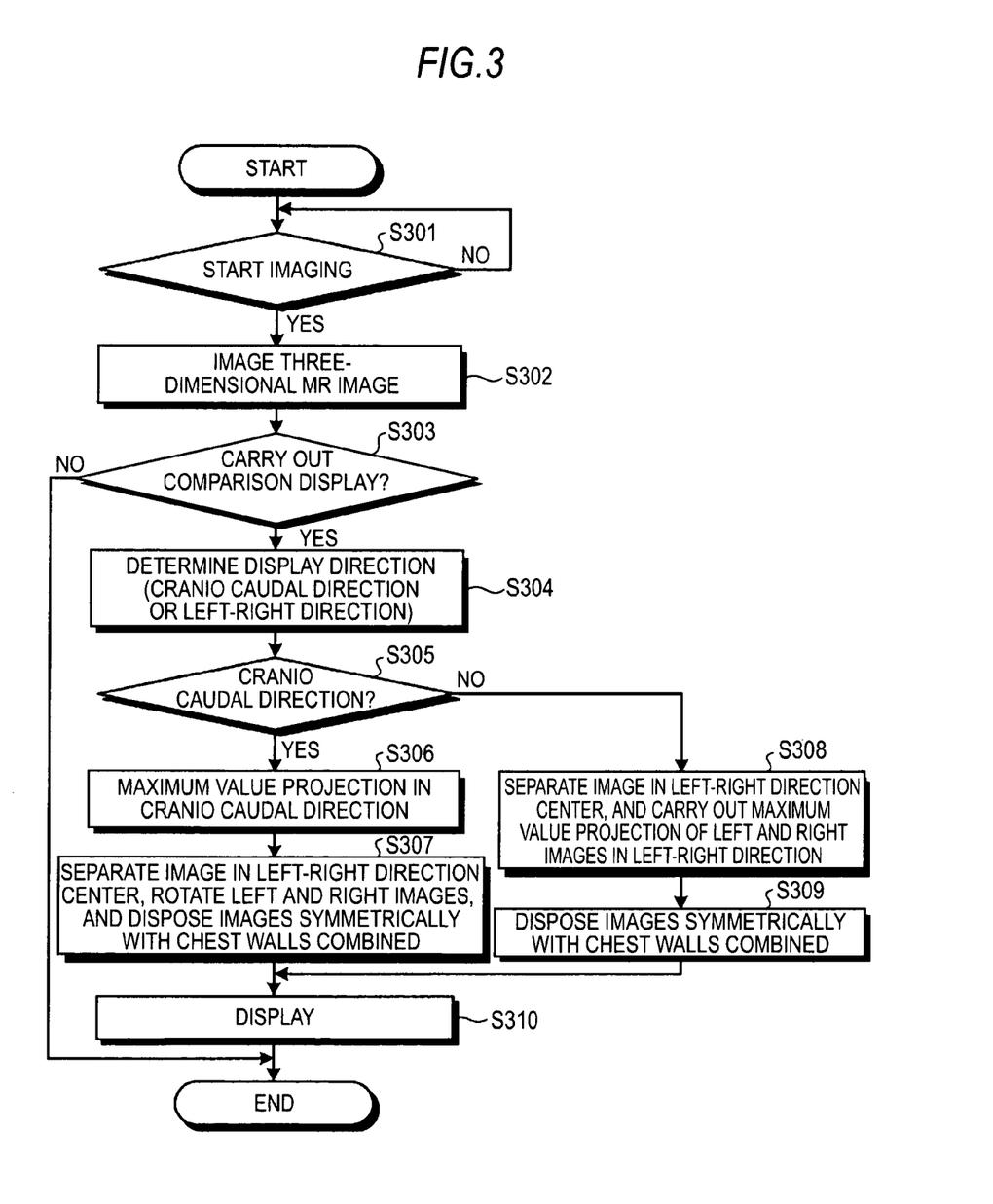
FIG. 3 is a simplified schematic flowchart illustrating an exemplary embodiment of processing steps for generating a comparison breast image using the MRI apparatus of FIG. 1.

Next, a description will be given, mainly using FIG. 3, of an exemplary processing procedure for generation of a CBI by MRI apparatus 100. FIG. 3 is a flowchart showing an exemplary processing procedure for generation of the CBI by MRI apparatus 100. A detailed description will be given of exemplary processes carried out by each unit included in the controlling unit 17 and data processing unit 13.

As shown in FIG. 3, in the MRI apparatus 100 according to the exemplary embodiment, computer system 10, when receiving a start instruction from the operator via input unit 16 (step S301, Yes), generates a three-dimensional image of the breasts of the subject P by appropriately controlling each unit of the MRI apparatus 100 (step S302).

Specifically, the sequence execution unit 17a, by controlling the gradient magnetic-field power supply 3, transmitter 7 and receiver 9, executes a desired imaging sequence for acquiring the magnetic resonance signal from a three-dimensional space including the left and right breasts of the subject. For example, sequence execution unit 17a may execute a gradient echo-cardiography imaging sequence wherein a one-dimensional frequency encode and a two-dimensional phase encode are combined. Also, data acquisition unit 12 acquires MR signal data transmitted from receiver 9 by executing the heretofore described imaging sequence. Then, image reconstruction unit 13a conventionally reconstructs a three-dimensional image data of the left and right breasts of the subject P by performing three-dimensional Fourier Transformation on the MR signal data acquired by data acquisition unit 12.

Normally, in order to prevent signal returning from an unnecessary region, data acquisition by the MRI apparatus is carried out from a region limited by being slice selected in one three-dimensional direction by a combination of an RF pulse whose bandwidth is limited and a slice-select gradient magnetic field. Imaging by acquiring data from a region limited by such slice-selection is called axial imaging, sagittal imaging, or coronal imaging according to the slice direction. Diagnosis using the MRI apparatus is carried out by saving and displaying each of axial, sagittal and coronal images, or images on which a maximum intensity projection (MIP) process is carried out along these axes. In general, axial or sagittal imaging is carried out in a breast examination. Therefore, hereafter, a description will be given of an exemplary case in which these two types of imagings are carried out.

In a mammary MRI examination, it may happen that an MR imaging agent is injected through a vein, and that an extent to which a region of interest is imaged, a time until the region is imaged, a time until the imaging agent flows out, and the like, are used as criteria for judgment on whether a tumor is benign or malignant. However, considering a time until the imaging agent is caused to flow outside the body, it is only possible to inject the imaging agent once for one examination, meaning that it is desirable to acquire images of both left- and right-side breasts in one three-dimensional imaging sequence.

Consequently, a rectangular parallelepiped region in which both left- and right-side breasts are included can be set when positioning is determined for an imaging region. When displaying three-dimensional image data obtained by subjecting raw acquired data to three-dimensional Fourier Transformation, in the case of axial imaging, anterior-posterior direction of the subject is the up-down direction of the image, and the left-right direction of the subject is the left-right direction of the image while, in the case of sagittal imaging, the superior-inferior direction of the subject is the up-down direction of the image, and the anterior-posterior direction of the subject is the left-right direction of the image.

In the case of axial imaging, it may happen that left and right breast images are saved and displayed in one image when the left and right breasts are imaged at one time but, in the case of sagittal imaging, the left and right breast are normally displayed as separate images. Such a common MR image display method differs from a method whereby a result of cranio-caudal (CC) imaging or medio-lateral (ML) imaging, or medio-lateral oblique (MLO) imaging, which is normally carried out by X-ray mammography, is read disposed with weight put on the symmetry of the left and right breasts, meaning that when carrying out a reading of the MR image in comparison with diagnosis information based on X-ray mammography diagnosis information, it is difficult to comprehend a proper positional relationship between the two images, the line of sight and the orientation of display where one of these orientations differ in one image from those of the other image.

Returning to the description of FIG. 3, after three-dimensional image data of the left and right breasts are reconstructed, CBI generation unit 13b determines whether or not to carry out a comparison display with an X-ray mammography image (step S303). At this time, for example, CBI generation unit 13b receives an operation of selecting one of a carrying out and non-carrying out of the comparison display, from the operator via input unit 16. Then, the CBI generation unit 13b, based on the received operator selection, determines whether or not to carry out a comparison display.

Herein, if it is determined not to carry out a comparison display (step S303, No), CBI generation unit 13b finishes the process without executing the procedure shown hereafter. Meanwhile, if it is determined to carry out a comparison display (step S303, Yes), CBI generation unit 13b determines a display direction in which the CBI is displayed (step S304).

Specifically, CBI generation unit 13b determines either a direction corresponding to the cranio-caudal direction (CC direction) in the X-ray mammography imaging or a direction corresponding to the lateral direction (ML direction or MLO direction) as the display direction in which the CBI is to be displayed. At this time, for example, CBI generation unit 13b receives an operation of selecting the direction in which the CBI is to be displayed, from the operator via input unit 16. Then, CBI generation unit 13b, based on the received operator selection, determines a CBI display direction.

If it is determined that the CBI is displayed in the cranio-caudal direction (step S305, Yes), CBI generation unit 13b, by performing an MIP process on three-dimensional image data generated by image reconstruction unit 13a, generates a two-dimensional projection image in which the left and right breasts are projected in the cranio-caudal direction (step S306). Also, CBI generation unit 13b separates the generated two-dimensional projection image in the left-right direction as compared to a center and, by combining chest wall portions of the separated left and right two-dimensional projection images, generates a CBI wherein the left and right breasts are disposed symmetrically with the chest walls combined (step S307).

Figure 4:
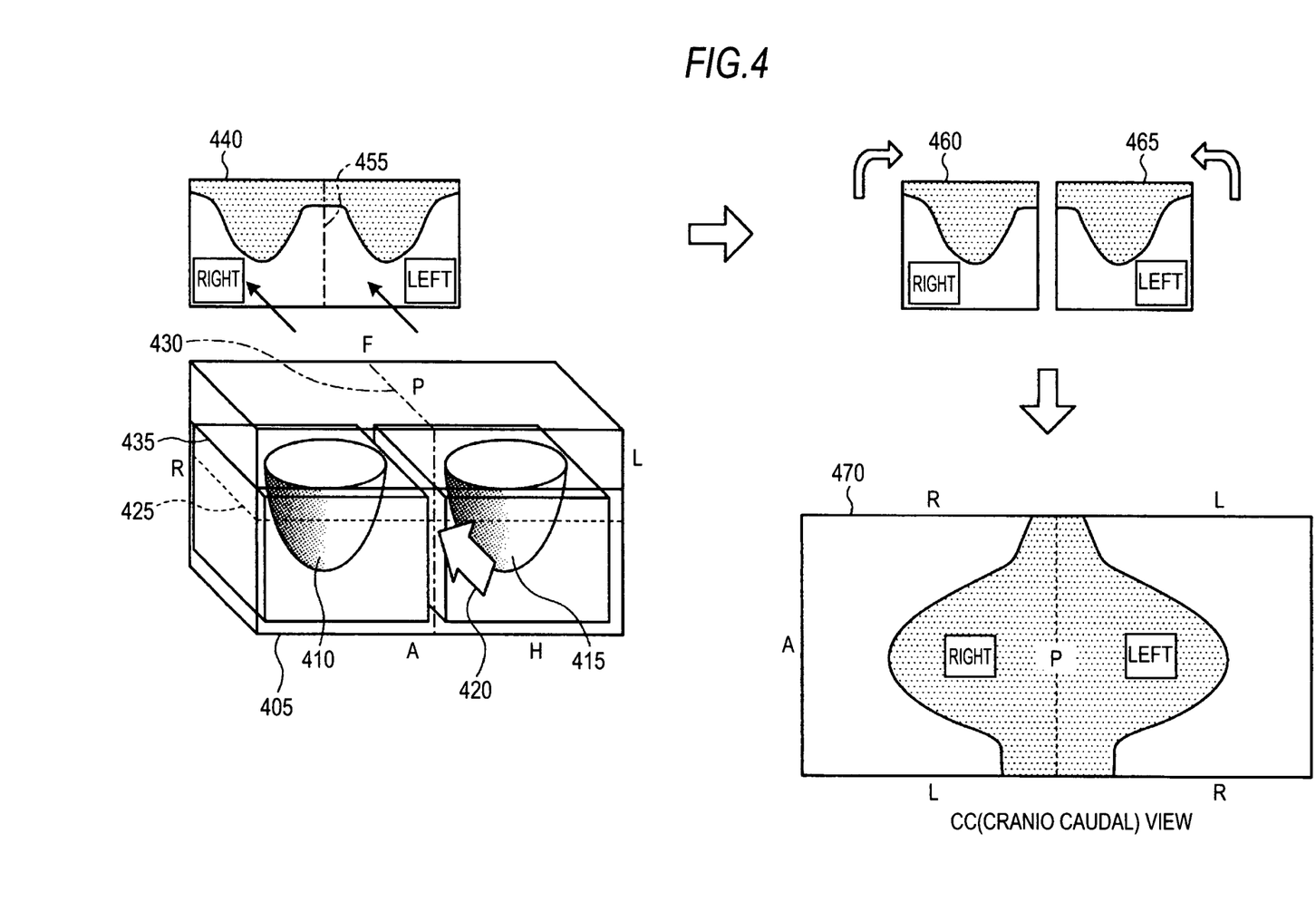
FIG. 4 is a simplified schematic diagram illustrating an exemplary embodiment for generation of a cranio-caudal direction comparison breast image by the comparison breast image generation unit of FIG. 2.

Herein, a specific description will be given, using FIG. 4, for generation of a cranio-caudal direction CBI by CBI generation unit 13b according to the exemplary embodiment. FIG. 4 is a diagram illustrating generation of a cranio-caudal direction comparison breast image by CBI generation unit 13b.

In FIG. 4, three-dimensional image data 405 are data generated by performing three-dimensional Fourier Transformation on MR signal data acquired by executing an imaging sequence using a three-dimensional imaging method. The three-dimensional image data 405 include a right breast 410 and a left breast 415. Also, A, P, R, L, H and F represent an anterior direction, a posterior direction, a right direction, a left direction, a head direction and a foot direction, respectively, in subject-domain coordinates.

Also, a dotted line 425 represents the vertical direction position of the upper end of the RF reception coil 8 or the upper end of the couch top plate 4a. Also, a dashed-dotted line 430 represents the left-right direction center of the apparatus-domain coordinate system. Herein, the dotted line 425 approximately coincides with the front side of the chest wall of the subject P. Also, the dashed-dotted line 430 approximately coincides with the center in the left-right direction relative to the axis of the subject P.

When generating the cranio-caudal direction comparison breast image, for example, CBI generation unit 13b carries out the MIP process in the head-foot (HF) direction shown by arrow 420, and creates a two-dimensional projection image which forms the comparison breast image. At this time, CBI generation unit 13b carries out the MIP process on a region 435 excluding a region on the back side (rear side) of a portion approximately corresponding to the chest wall. Herein, the right breast 410 and left breast 415 in FIG. 4 are shown completely separated for convenience of drawing. However, actually, region 435 is a region including the chest wall, as heretofore described. Consequently, the right breast 410 and left breast 415 shall be understood to actually be connected in the vicinity of dotted line 425. The same also applies in FIGS. 5-7.

Herein, with the vertical direction position of the RF reception coil 8 or couch top plate 4a as a reference, for example, as shown by dotted line 425, a position a certain width away from the reference position toward the back side is set as a boundary between region 435 in which the MIP process is carried out and the excluded region. Because of this, it is possible to appropriately set a range in which the MIP process is carried out. Also, by setting a predetermined range using this method, it is possible to select only a region including one portion of the breasts and chest wall, and exclude regions such as the lungs and heart unnecessary in diagnosis.

The regional selection and exclusion, not being limited to those with the position of the RF reception coil 8 or couch top plate 4a as the reference, also may be carried out using image recognition. In this case, for example, region 435 is selected by pattern recognition of the left and right breasts. More specifically, for example, a configuration may be such that changes in the lateral direction size of the left and right breasts from the front side to the rear side of the subject is recognized and, as the left and right breasts come closer and are connected in the vicinity of the chest wall, this connected position is recognized as the position of the chest wall, thus automatically selecting region 435 in which the MIP process is carried out.

Herein, a description has been given of a case in which CBI generation unit 13b carries out the MIP process in the limited region of three-dimensional image data 405. Apart from this, for example, a configuration may be such that CBI generation unit 13b carries out the MIP process in the whole region of three-dimensional image data 405 and, subsequently, deletes an unnecessary region from a two-dimensional image obtained by the MIP process.

Then, after carrying out the MIP process, CBI generation unit 13b separates a two-dimensional projection image 440 obtained by the MIP process using a line 455 corresponding to the left-right direction center of apparatus-domain coordinates. Continuing, CBI generation unit 13b rotates an image 460, of the separated two images, including the right breast through 90 degrees in a clockwise direction, and rotates an image 465 including the left breast through 90 degrees in a counter-clockwise direction. Subsequently, CBI generation unit 13b generates a comparison breast image 470 by combining the individual rotated images in such a way as to be symmetrical (e.g., with their chest walls combined if desired so as to more closely simulate an X-ray mammography image).

Provided that the position of subject P is set in such a way that the center in the left-right direction relative to the axis of subject P coincides with the left-right direction center of the apparatus coordinates when the subject P is placed on couch 4, when the image is separated into left and right in a position corresponding to the left-right direction center of the apparatus-domain coordinates, symmetry of the left and right breasts in the up-down direction, that is, in the left-right direction of the subject, of the combined image is maintained. Because of this, the resulting comparison breast image 470 is such that the line of sight and direction thereof coincide with the display method when carrying out a comparison reading with the two images, obtained in the CC direction imaging by X-ray mammography apparatus, disposed symmetrically. Consequently, it is easier to carry out a comparison of the X-ray mammography and MR images.

Herein, comparison of the X-ray mammography image and MR image may be carried out by comparing images respectively displayed on each of different display units, but the exemplary embodiment is not limited to this. For example, display control unit 17b may adjust sizes of a mammography image obtained from outside the MRI system and the MRI comparison breast image 470 in such a way as to be of the same scale, and then display both images on the same display unit 15. Specifically, display control unit 17b may compare sizes of the X-ray mammography image and MRI comparison breast image 470 with their respective full scales and, by scaling up or down at least one of the images, adjust the images in such a way that the breasts are displayed at the same size. A specific display form may be such that the X-ray mammography image and MRI comparison breast image 470 are disposed adjacent to each other and in parallel, or one of them may be displayed by switched alternate displays in accordance with an instruction input into input unit 16.

Returning to the description of FIG. 3, if it is determined that the comparison breast image is to be displayed in the left-right direction (step S305, No), CBI generation unit 13b, by performing the MIP process on three-dimensional image data generated by image reconstruction unit 13a in the left and right directions from the center of the three-dimensional image data, generates two-dimensional MIP images in which each of the left and right breasts is projected (step S308). Also, CBI generation unit 13b, by combining chest wall portions of the generated two-dimensional projection images (if desired), generates a comparison breast image wherein the left and right breasts are disposed symmetrically with the chest walls combined (step S309).

Figure 5:
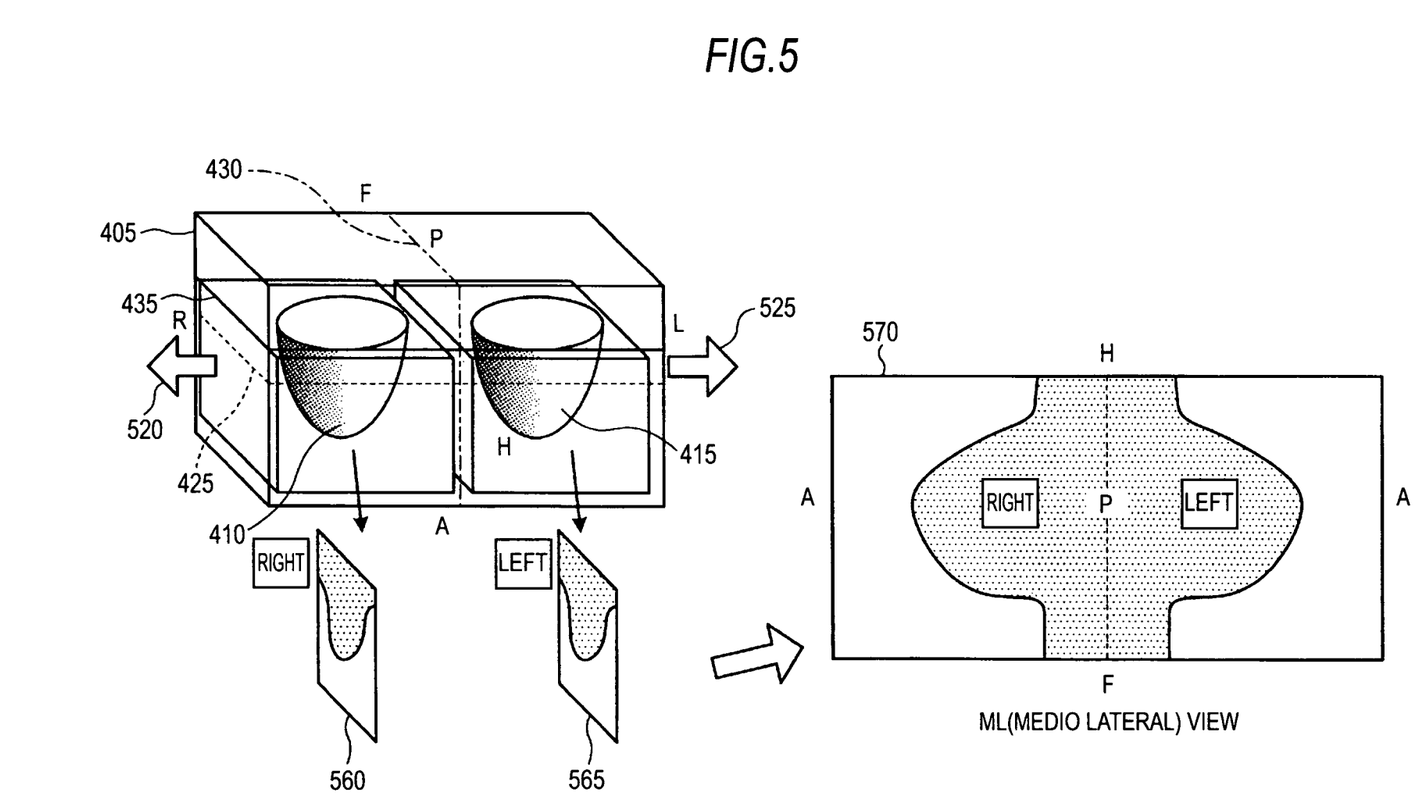
FIG. 5 is a simplified schematic diagram illustrating an exemplary embodiment for generation of a left-right direction comparison breast image by the comparison breast image generation unit of FIG. 2.

Herein, a specific description will be given, using FIG. 5, for generation of a left-right direction comparison breast image by CBI generation unit 13b according to the exemplary embodiment. Three-dimensional image data 405 shown in FIG. 5 are the same as those shown in FIG. 4.

When generating the left-right direction comparison breast image, for example, CBI generation unit 13b carries out the MIP process on a region 435 excluding a region on the back side (rear side) of a portion approximately corresponding to the chest wall, in the same way as in the case of generating a head-foot direction comparison breast image. That is, CBI generation unit 13b carries out the MIP process on a region on the front side of a boundary line corresponding to the chest wall but, in this case, the region 435 is divided in two by a dashed-dotted line 430 representing the left-right direction center of the apparatus coordinates, and the individual regions are projected at the maximum value in the left and right directions shown by arrows 520 and 525, respectively. Because of this, it is possible to obtain a left-right direction two-dimensional projection image 560 of the right breast and a left-right direction two-dimensional projection image 565 of the left breast.

Then, after carrying out the MIP process, CBI generation unit 13b generates the CBI 570 by rotating and combining the two-dimensional projection image 560 and two-dimensional projection image 565 obtained by the MIP process in such a way that the chest walls thereof are combined (if desired). By so doing, the obtained CBI 570 is such that the line of sight and direction thereof approximately coincide with the display method when reading with the two X-ray mammography images acquired by the ML direction or MLO direction imaging disposed symmetrically.

Returning to FIG. 3, when the comparison breast image is generated by CBI generation unit 13b, the display control unit 17b causes display unit 15 to display the generated CBI (step S310).

As heretofore described, in the exemplary embodiment, sequence execution unit 17a executes the imaging sequence for acquiring MR signal from a three-dimensional space including the left and right breasts of subject P. Also, image reconstruction unit 13a reconstructs a three-dimensional image data of the left and right breasts based on the MR signal acquired by sequence execution unit 17a executing the selected imaging sequence. Also, CBI generation unit 13b generates the two-dimensional images, one each of the left and right breasts, from the three-dimensional image data reconstructed by image reconstruction unit 13a and, by combining chest wall portions of the generated individual two-dimensional images, generates a CBI with the left and right breasts disposed symmetrically. Then, display control unit 17b causes display unit 15 to display the comparison breast image generated by CBI generation unit 13b.

In this way, in the exemplary embodiment, the breast is imaged by the MRI apparatus 100, in the same general geometric way as the X-ray mammography image and can be displayed with the left and right breasts being disposed symmetrically (with chest walls combined if desired to more closely parallel X-ray mammography images). Consequently, according to the exemplary embodiment, it is possible to provide the reader with an MR image that facilitates comparison with an X-ray mammography image. Also, according to the exemplary embodiment, as it is easy to compare the X-ray mammography image and MR image, it is also possible to carry out a diagnosis such as by determining a position of micro-calcification from mammography, and MR searching for invasive ductal breast cancer in approximately the same region.

In the exemplary embodiment, a description has been given of a case in which the two-dimensional images of the breasts are generated by carrying out the MIP process on three-dimensional image data, and the comparison breast image is generated using the two-dimensional images. However, the comparison breast image is not limited to this technique.

For example, minimum intensity projection and/or value averaging (adding) projection processes can be used, as can any process for converting three-dimensional MR image data to two-dimensional images. In addition, the method of generating the comparison breast image does not necessarily include a process, such as the projection process, of converting three-dimensional MR image data to two-dimensional images.

For example, a configuration may be such that the CBI generation unit 13b generates a plurality of axially cut cross-sectional MR images arranged in the left-right direction of subject P from three-dimensional MR image data reconstructed by image reconstruction unit 13a, divides the thusly generated plurality of cross-sectional images into two image groups in opposite directions from the left-right direction center (and, if desired, combines the chest wall portion of each cross-sectional image included in the left-side image group and the chest wall portion of each corresponding cross-sectional image included in the right-side image), thereby generating a plurality of comparison breast images.

Figure 6:
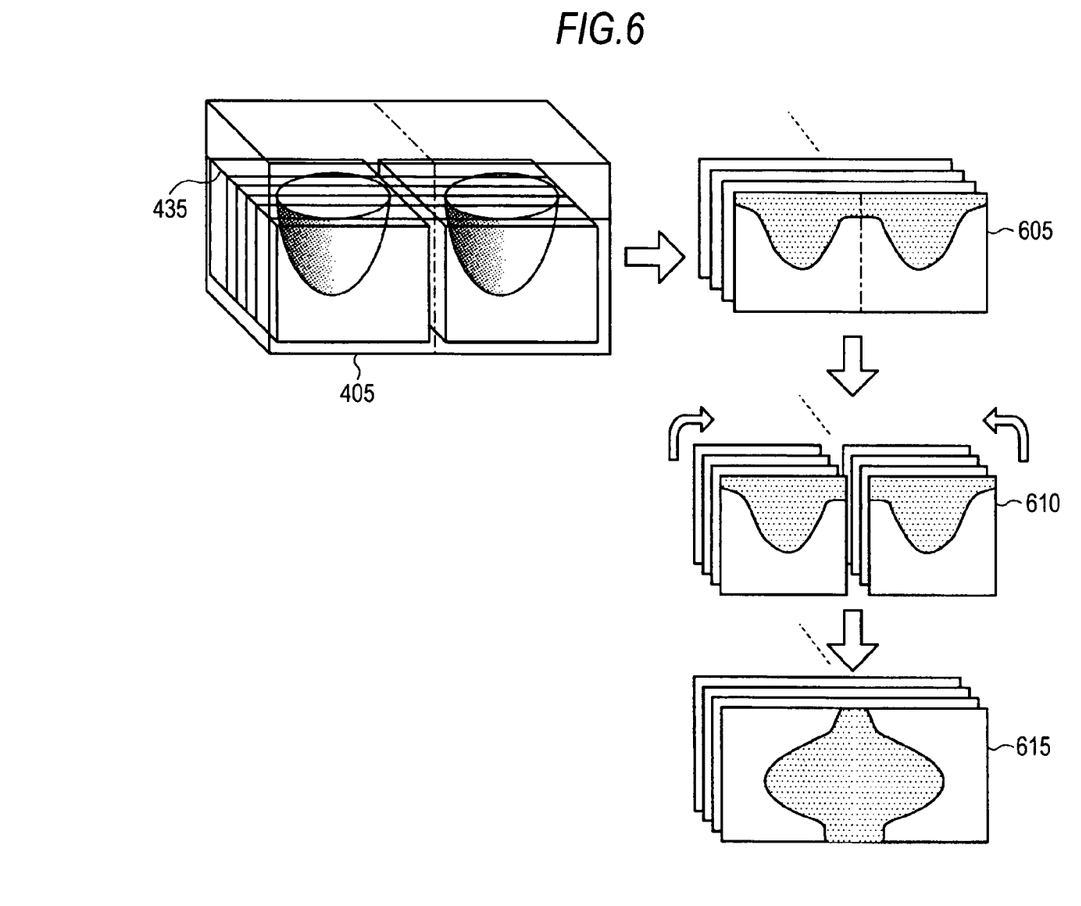
FIG. 6 is a simplified schematic diagram illustrating an exemplary embodiment for generation of a cranio-caudal direction comparison image by the comparison breast image generation unit according to another embodiment.

FIG. 6 is a diagram illustrating generation of a craniocaudal direction comparison image by CBI generation unit 13b according to another exemplary embodiment. In this case, CBI generation unit 13b selects regions of axially cut cross-sectional images from three-dimensional image data generated by image reconstruction unit 13a, cuts out cross-sectional images, separates each cut-out cross-sectional image into left and right groups, and rotates and combines the left and right images.

At this time, CBI generation unit 13*b* obtains a two-dimensional image group 605 by cutting out a plurality of axially cut cross-sectional images from, for example, region 435, among regions included in three-dimensional image data 405 shown in FIG. 6, excluding a region on the back side of a portion approximately corresponding to the chest wall. Then, CBI generation unit 13*b*, after halving the obtained image group 605 in the left-right direction center of the apparatus coordinates, rotates halved image groups 610, and combines the left- and right-sides thereof, thereby generating a CBI group 615. Because of this, it is possible to obtain a plurality of comparison breast images of which the line of sight and direction coincide with the display method when carrying out a reading with two images, acquired by the CC direction imaging by X-ray mammography, disposed symmetrically.

Also, for example, a configuration may be such that CBI generation unit 13*b* creates a plurality of sagittally cut cross-sectional images arranged in the cranio-caudal direction of subject P from the three-dimensional image data reconstructed by image reconstruction unit 13*a* and, if desired, combines the chest wall portions of each pair of images, among the created plurality of cross-sectional images, positioned the same distance from the center of the three-dimensional image data, thereby generating a plurality of comparison breast images.

Figure 7:
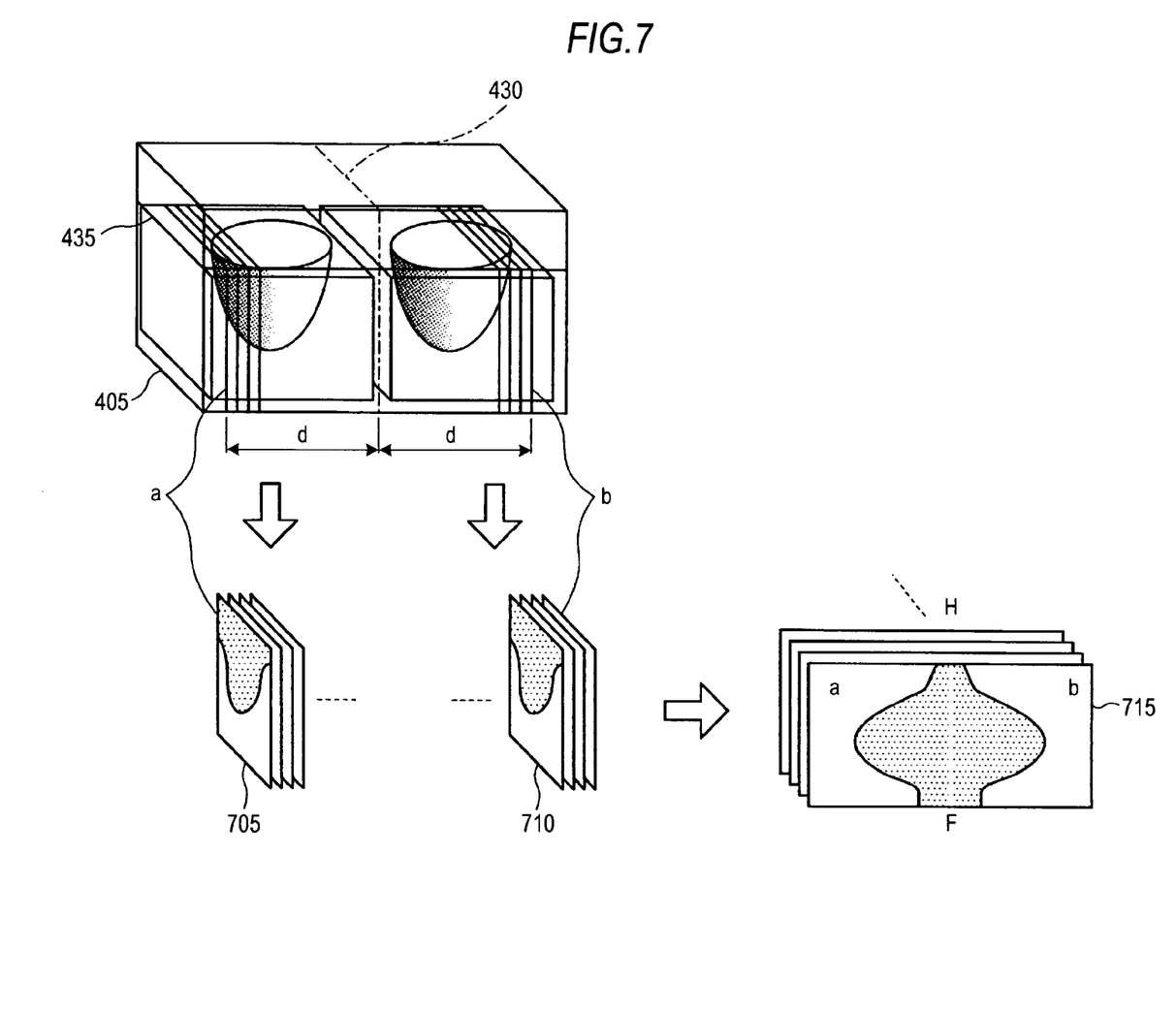
FIG. 7 is a simplified schematic diagram illustrating an exemplary embodiment for generation of a left-right direction comparison breast image by the comparison breast image generation unit according to another embodiment.

FIG. 7 is a diagram illustrating generation of left-right comparison breast images by CBI generation unit 13*b* according to another embodiment. In this case, CBI generation unit 13*b* selects regions of sagittally cut cross-sectional images from three-dimensional image data generated by image reconstruction unit 13*a*, cuts out the cross-sectional images, and rotates and combines the cut-out cross-sectional images for every two two-dimensional images with an equal distance from the left-right direction center of the apparatus coordinates.

At this time, CBI generation unit 13*b* obtains two-dimensional images by cutting out the plurality of sagittally cut cross-sectional images from, for example, region 435, among regions included in three-dimensional image data 405 shown in FIG. 7, excluding a region on the back side of a portion approximately corresponding to the chest wall. Then, CBI generation unit 13*b*, by dividing the obtained images in a left-right direction center 430 of the apparatus coordinates, divides the two-dimensional images into image group 705 and image group 710. In the example shown in FIG. 7, image group 705 forms a set of two-dimensional images including the right-side breast, and image group 710 forms a set of two-dimensional images including the left-side breast.

Subsequently, CBI generation unit 13*b* generates comparison breast images by selecting images with an equal distance from the left-right direction center 430 of the apparatus coordinates, one from each of image group 705 and image group 710, and combining each selected pair of images in such a way that the chest walls of the pair of images are combined (if desired) coinciding in the cranio-caudal direction of subject P. For example, as shown in FIG. 7, CBI generation unit 13*b* creates one comparison image using image data a and b positioned distance d away from the left-right direction center 430 of the apparatus coordinates. CBI generation unit 13*b* generates a CBI group 715 by carrying out the same process for each pair of images positioned an equal distance from the left-right center 430 of the apparatus coordinates. Because of this, it is possible to obtain a plurality of comparison breast images in which the line of sight and direction approximately coincide with the display of images acquired by the ML direction or MLO direction X-ray mammography, disposed symmetrically.

In the heretofore described exemplary embodiments, a description has been given of a case in which three-dimensional image data are reconstructed by performing three-dimensional Fourier Transformation on MR signals acquired from three-dimensional space, and a comparison breast image is generated using the three-dimensional image data. However, other approaches are also feasible. For example, it is also possible to use, for example, volume data obtained by carrying out two-dimensional multi-slice imaging.

Also, in mammary MR examination, it may happen that the MRI apparatus carries out continuous imaging in order to recognize a change of a signal value of tissues after injecting an imaging agent, generates a change curve of a signal value with respect to time (a time intensity curve) in each of pixels of time-series images obtained by the continuous imaging, generates images wherein values indicating a curve inclination, a time at which the signal value reaches a maximum value, and the like, in the change curve are correlated with the colors of the pixels, and provides the images as diagnostic images. Image data wherein some post-processing is performed on images, such as so-called color map images, reconstructed from the MR signal can also be displayed, by carrying out thereon the process described in the heretofore described exemplary embodiments, as a two-dimensional image wherein the left and right breasts are disposed symmetrically (including combining chest wall portions of the two-dimensional images of the left and right breasts, if desired).

Also, with MRI apparatus, it is possible to generate images of properties differing depending on various MRI sequences. For example, there may be a T1-weighted image, a T2-weighted image, and the like, and images of tissues thusly weighted differ from one another. Apart from this, various blood vessel-weighted images obtained by imaging and non-imaging can be provided. It is also possible to generate image weighting a signal with a low diffusion coefficient, which is called a diffusion-weighted image. The diffusion-weighted image, as it can weight tissues with a high density, can be said to be suitable for detecting a malignant tumor, and is useful for a breast tumor diagnosis. In the exemplary embodiments, it is possible to use images of various properties, including the heretofore described ones. In this case, a two-dimensional image is generated wherein a region in which the MIP or other projection is carried out in the way heretofore described onto each of the plurality of images of various properties is selected, and the left and right breasts are disposed symmetrically (and with the chest wall portions combined, if desired).

In addition, it may happen that diagnostic information that cannot be obtained with a single image can be obtained by comparing and observing images of differing properties. Consequently, in the exemplary embodiments, display control unit 17*b* may display each image in a display form in which it is also possible to compare an X-ray mammography image and a plurality of different kinds of MR images. As a specific example of comparable display, the entire X-ray mammography image and a plurality of MR images may be displayed in parallel. Also, any one of the X-ray mammography image and a plurality of MR images may be displayed at one time, and the display switched to different images by a predetermined input into input unit 16. Furthermore, two images, one of the plurality of MR images and the X-ray mammography image, may be displayed at one time, and the plurality of MR images displayed as switched by a predetermined input into input unit 16. Also, when generating the plurality of kinds of comparison breast images shown in FIGS. 6 and 7, and when displaying a plurality of MR images, it is desirable to effect control in such a way that a plurality of MR images corresponding to the same positions are always displayed.

Also, in the heretofore described exemplary embodiments, it has been described that the MR image can be displayed as a two-dimensional image wherein the left and right breasts are disposed symmetrically by combining the chest wall portions of the two-dimensional images of the left and right breasts. However, the chest wall portion used herein does not necessarily indicate only a portion in which the chest wall is exposed, but may be a portion which is slightly inside the chest wall and actually does not include the chest wall. The point is that it is sufficient that a region comparable with the range of imaging by the X-ray mammography apparatus be displayed. Therefore, it is possible that the chest wall portions of left and right breasts may not be combined. For example, the two-dimensional images may be disposed so that the chest walls are disposed substantially parallel to each other at a some (or no) distance from each other.

Also, in the heretofore described exemplary embodiments, a description has been given of a case in which MRI apparatus 100 is used, but the comparison image display process can also be similarly applied to, for example, an image processing apparatus connected to the MRI apparatus 100 via a network. In this case, an MRI apparatus 100 (or the like, possibly storing an archive of past-acquired MRI data) transfers three-dimensional MR signal data or three-dimensional image data, which are a source of data for generating the comparison breast image, to the image processing apparatus by way of the network or via a data recording medium. Then, the image processing apparatus, based on the three-dimensional MR signal data or three-dimensional image data transferred from the MRI apparatus, carries out the same process as the computer system 10 described in the heretofore described exemplary embodiments, and thereby generates and displays the comparison breast image.

Also, all or one portion of the functions of sequence execution unit 17a, display control unit 17b, image reconstruction unit 13a and CBI generation unit 13b described in the exemplary embodiments can also be realized, at least in part, by suitable software modules. That is, the functions of the heretofore described units are realized by causing a computer to execute an image processing program regulating the exemplary processing procedure shown in FIG. 3. At this time, the image processing program may be installed in advance in the computer, may be recorded in a removable recording medium, such as a magnetic disk, a magneto-optical disk, an optical disk, or a semiconductor memory, or may be distributed via a network, and installed in a computer apparatus as appropriate.

Also, in the heretofore described exemplary embodiments, a description has been given of a case in which MRI apparatus 100 is used, but the comparison image process can also be similarly applied to another medical diagnostic imaging apparatus such as, for example, an X-ray CT apparatus or a PET apparatus, other than an X-ray mammography apparatus.

While certain embodiments have been described, these embodiments have been presented by way of example only, and are not intended to limit the scope of the inventions. Indeed, the novel methods and systems described herein may be embodied in a variety of other forms. Furthermore, various omissions, substitutions and changes in the form of the methods and systems described herein may be made without departing from the spirit of the inventions. The accompanying claims and their equivalents are intended to cover such forms or modifications as would fall within the scope and spirit of the inventions.

What is claimed is:

1. An image processing apparatus comprising:
a generation unit configured to
acquire a single three-dimensional magnetic resonance (MR) image of patient anatomy including both left and right breasts of the patient;
project said three-dimensional MR image data to generate at least two two-dimensional images which respectively represent the left and right breasts of said patient; and
generate a comparison two-dimensional composite MR image of the left and right breasts for comparison to a composite X-ray mammography image having symmetrically disposed left and right breast images therewithin, wherein the two-dimensional left and right breast MR images are disposed symmetrically in the comparison two-dimensional composite MR image like those in the X-ray mammography image; and
a display control unit configured to display the comparison two-dimensional image on a display unit.

2. The image processing apparatus according to claim 1, wherein the generation unit is further configured:
to generate the two-dimensional left and right images using a data projection process along a superior-inferior direction or an anterior-posterior direction within said three-dimensional image data.

3. The image processing apparatus according to claim 2, wherein the data projection process includes at least one of (a) maximum intensity projection, (b) minimum intensity projection, and (c) value averaging projection.

4. The image processing apparatus according to claim 2, wherein the generation unit is further configured:
to carry out the projection process on a region excluding a region on the back side of a portion approximately corresponding to the chest wall.

5. The image processing apparatus according to claim 1, wherein the generation unit is further configured:
to generate a plurality of axial cross-sectional images arranged in left-right direction of the subject from the three-dimensional image data,
to cut the axial cross-sectional images at a left-right direction center into two image groups of cross-sectional images, and
to generate a plurality of comparison two-dimensional images based on combining chest wall portions of the cross-sectional images in the right-side image group and the cross-sectional images in the left-side image group.

6. The image processing apparatus according to claim 1, wherein the generation unit is further configured:
to generate a plurality of sagittal cross-sectional images arranged in a cranio-caudal direction of the subject from the three-dimensional image data, and
to generate a plurality of comparison two-dimensional images based on combining chest wall portions of each pair of images, among the plurality of sagittal cross-sectional images, positioned at a same distance from a center of the three-dimensional image data.

7. The image processing apparatus according to claim 1, wherein the three-dimensional image data is acquired by MRI apparatus.

8. The image processing apparatus according to claim 7, wherein:
the generation unit is further configured to generate a plurality of different kinds of comparison two-dimensional images which are respectively based on a corresponding plurality of different kinds of three-dimensional image data, and the display control unit is further configured to display the plurality of different kinds of comparison two-dimensional images to facilitate comparisons therebetween.

9. The image processing apparatus according to claim 1, wherein the display control unit is further configured:
to display an X-ray mammography image so that comparison of the X-ray mammography image and the comparison two-dimensional image is facilitated.

10. The image processing apparatus according to claim 1, further comprising:
a couch configured to support the subject;
an RF reception coil disposed on said couch and configured to receive NMR RF response signals emanating from the subject; and
a reconstruction unit configured to reconstruct the three-dimensional image data based on the NMR RF response signals received by the RF reception coil, and
wherein the generation unit is further configured to recognize a position of a breast wall based on the position of the couch or the RF reception coil.

11. The image processing apparatus according to claim 1, wherein the comparison two-dimensional image includes combined chest wall portions of the two-dimensional left and right breast images.

12. An image processing method comprising:
acquiring a single three-dimensional magnetic resonance (MR) image of patient anatomy including both left and right breasts of a patient;
projecting said three-dimensional MR image data to generate at least two two-dimensional images which respectively represent the left and right breasts of said patient;
generating a comparison two-dimensional composite MR image of the left and the right breasts for comparison to a composite X-ray mammography image having symmetrically disposed left and right breast images therewithin, wherein the left and right breast MR images are disposed symmetrically in the comparison two-dimensional composite MR image like those in the X-ray mammography image; and
displaying the comparison two-dimensional image on a display unit.

13. The image processing method according to claim 12, further comprising:
generating the two-dimensional images of the left and right breasts using a data projection process along a superior-inferior direction or an anterior-posterior direction within said three-dimensional image data.

14. The image processing method according to claim 13, wherein the projection process includes at least one of (a) maximum intensity projection, (b) minimum intensity projection, and (c) value averaging projection.

15. The image processing method according to claim 13, further comprising:
carrying out the projection process on a region excluding a region on the back side of a portion approximately corresponding to the chest wall.

16. The image processing method according to claim 12, further comprising:
generating a plurality of axial cross-sectional images arranged in left-right direction of the subject from the three-dimensional image data,
cutting the axial cross-sectional images at a left-right direction center into two image groups of cross-sectional images, and
generating a plurality of the comparison two-dimensional images based on combining chest wall portions of the cross-sectional images in the right-side image group and the cross-sectional images in the left-side image group.

17. The image processing method according to claim 12, further comprising:
generating a plurality of sagittal cross-sectional images arranged in a cranio-caudal direction of the subject from the three-dimensional image data, and
generating a plurality of the comparison two-dimensional images of each pair of images among the plurality of sagittal cross-sectional images positioned at a same distance from a center of the three-dimensional image data.

18. The image processing method according to claim 12, wherein the three-dimensional image data is acquired by MRI apparatus.

19. The image processing method according to claim 18, further comprising:
generating a plurality of different kinds of the comparison two-dimensional images which are respectively based on a corresponding plurality of different kinds of three-dimensional image data, and
displaying the plurality of different kinds of comparison two-dimensional images so as to facilitate comparisons therebetween.

20. The image processing method according to claim 12, further comprising:
displaying an X-ray mammography image so that comparison of the X-ray mammography image and the comparison two-dimensional image is facilitated.

21. The image processing method according to claim 12, further comprising:
supporting the subject on a couch;
receiving NMR RF response signals emanating from the subject by an RF reception coil disposed on the couch;
reconstructing the three-dimensional image data based on the NMR RF response signals received by the RF reception coil, and
recognizing a position of a breast wall based on the position of the couch or the RF reception coil.

22. The image processing apparatus according to claim 12, wherein the comparison two-dimensional image includes combined chest wall portions of the two-dimensional left and right breast images.

* * * * *